United States Patent [19]

Kawada et al.

[11] Patent Number: 4,754,026
[45] Date of Patent: Jun. 28, 1988

[54] CONVERSION OF URACIL DERIVATIVES TO CYTOSINE DERIVATIVES

[75] Inventors: Mitsuru Kawada, Amagasaki; Kiyoharu Matsumoto, Kawachinagano; Masaaki Tsurushima, Minoo, all of Japan

[73] Assignee: Takeda Chemical Industries, Ltd., Osaka, Japan

[21] Appl. No.: 866,960

[22] Filed: May 27, 1986

[30] Foreign Application Priority Data

Jun. 4, 1985 [JP] Japan .............................. 60-121786
Feb. 5, 1986 [JP] Japan .............................. 61-24640

[51] Int. Cl.[4] ................... C07H 19/067; C07H 19/00
[52] U.S. Cl. ...................................... 536/23; 536/122
[58] Field of Search .................... 536/23, 122; 514/49

[56] References Cited

FOREIGN PATENT DOCUMENTS 0140254  2/1980  Fed. Rep. of Germany ........ 514/49
2122991  6/1982  Fed. Rep. of Germany .

OTHER PUBLICATIONS

Heinzscheit, Nucleotide Analogs, Syn. & Biological Function, Wiley-Interscience Publication, 1980.
Fox et al., J.A.C.S., 81, pp. 178-187 (1959).
Kaneko et al., Chem. Pharm. Bull., 20, pp. 1050-1053 (1972).

Primary Examiner—Anton H. Sutto
Assistant Examiner—Jenny Tou
Attorney, Agent, or Firm—Wenderoth, Lind & Ponack

[57] ABSTRACT

A process is disclosed for producing a 4-O-sulfonyluracil derivative of the formula

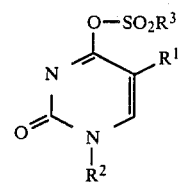

[wherein $R^1$ is hydrogen, halogen, alkyl and alkoxy, $R^2$ is glycosyl having protected hydroxyls; and $-SO_2R^3$ is an organic sulfonyl] which comprises reacting an uracil derivative of the formula

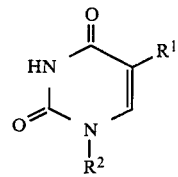

[wherein $R^1$ and $R^2$ are as defined above] with an organic sulfonylating agent of the formula $R^3SO_2X$ [wherein $R^3SO_2$ is an organic sulfonyl and X is halogen] in the presence of potassium carbonate. The obtained 4-O-sulfonyluracil is further subjected to amination. The processes are industrially adavantageous and produce cytosine derivatives such as cytidine in high yield.

18 Claims, No Drawings

CONVERSION OF URACIL DERIVATIVES TO CYTOSINE DERIVATIVES

This invention relates to the production of 4-O-organic sulfonyluracil derivatives and the conversion thereof to cytosine derivatives which are useful as intermediates for production of drugs such as cytidine diphosphate choline whose generic name is Citicoline.

For production of cytosine glycoside derivatives such as cytidine, various methods using uracil glycoside derivatives as the starting material have hitherto been known.

Proposed procedures include: (i) a procedure where uridine derivatives with protected hydroxyl groups in the sugar moiety are allowed to react with phosphorus pentasulfide to give 4-thio derivatives, which are then aminated at the position 4 by the reaction with ammonia or other materials and subjected to elimination of the protecting groups, to give cytidine derivatives (J. Amer. Chem. Soc., 81, 178 (1959).), (ii) a procedure where uridine or uridine derivatives with protected hydroxyl groups are allowed to react with a silylating agent such as hexamethyldisilazane (HMDS) to give 4-O-trimethyl-silyluridine derivatives which are then aminated at the position 4 by the reaction with ammonia or other materials and subjected to elimination of the protecting groups, to give cytidine derivatives (FRG Patent No. 2122991 Specification), (iii) a procedure where uridine with protected hydroxyl groups is subjected to chlorination with phosphorous oxychloride in the presence of diethylaniline hydrochloride as a catalyst to give cytidine (Chem. Pharm. Bull., 20, 1050 (1972)) and (iv) a procedure where a uridine derivative with protected hydroxyl groups is allowed to react with an organic sulfonylating agent in the presence of sodium hydride to give a 4-O-sulfonyluridine derivative which is then aminated at the position 4 by, e.g., ammonia, and subjected to elimination of the protecting groups, to give cytidine derivatives (GDR Pat. No. 140,254 Official Gazette (1980)).

However, these procedures are industrially disadvantageous because of the not necessarily satisfactory yield of the desired substances and of the use of an inflammable agent difficult to handle such as sodium hydride.

As a result of our research to establish industrially advantageous procedures for production of 4-O-sulfonyluridine derivatives by the reaction of uridine derivatives with protected hydroxyl groups in the sugar moiety with organic sulfonylating agents, we found that, when potassium carbonate is used as an acid-eliminating agent in the sulfonylation, 4-O-sulfonyl derivatives are obtained almost quantitatively. The specific action of potassium carbonate was surprising, seeing that sulfonylation did not proceed sufficiently with an alkali such as sodium carbonate as the acid-eliminating agent. This invention is based on these findings.

Thus, this invention relates to (1) a process for producing 4-O-sulfonyluracil derivatives having the general formula

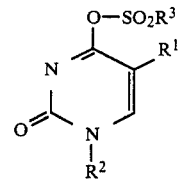

(III)

[wherein $R^1$ is a hydrogen atom, a halogen atom, an alkyl group or an alkoxyl group, $R^2$ is a glycosyl group with protected hydroxyl groups, and $R^3SO_2$ is an organic sulfonyl group], which comprises reacting uracil derivatives having the general formula

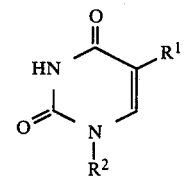

(I)

[wherein $R^1$ and $R^2$ are the same as described above] with an organic sulfonylating agent (II) having the general formula $R^3SO_2X$ [wherein $R^3SO_2$ is an organic sulfonyl group and X is a halogen atom] in the presence of potassium carbonate, and (2) a process for producing cytosine derivatives which comprises subjecting 4-O-sulfonyluracil derivatives having the general formula

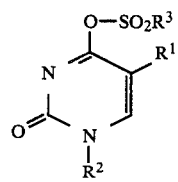

(III)

[wherein $R^1$ is a hydrogen atom, a halogen atom, and alkyl group or an alkoxyl group, $R^2$ is a glycosyl group with protected hydroxyl groups, and $R^3SO_2$ is an organic sulfonyl group] to amination.

In the procedure according to this invention, uracil derivatives (I) are used as the starting substances. The halogen referred to in the definition of $R^1$ includes fluorine and chlorine, the alkyl groups include lower alkyl groups with 1 to 6 carbon atoms such as methyl, ethyl, n-propyl, and n-butyl, and the alkoxyl groups include lower alkoxyl groups with 1 to 6 carbon atoms such as methoxyl, ethoxyl, n-propoxyl, and n-butoxyl. The lower alkyl groups may be substituted with hydroxyl group, amino group or halogen atom such as fluorine and chlorine. The glycosyl group referred to in the definition of $R^2$ includes furanosyl groups such as ribofuranosyl, deoxyribofuranosyl, arabinofuranosyl and glucofuranosyl, and pyranosyl groups such as ribopyranosyl, deoxyribopyranosyl, arabinopyranosyl, and glucopyranosyl. These glycosyl groups may be bound to bases through α- or β-linkage. The hydroxyl groups in these glycosyl groups are protected with protecting groups usually used for protection of the hydroxyl groups in the sugar, such as acyl (e.g. acetyl, benzoyl) and benzyl.

Such uracil derivatives (I) are exemplified by uridine with protected hydroxyl groups in the sugar moiety, and uracil nucleosides such as 5-fluoro-1-(β-D-ribofuranosyl)uracil, 5-methyl-1-(β-D-ribofuranosyl)uracil, 1-β-D-arabinofuranosyluracil, and 1-(2'-deoxy-β-D-ribofuranosyl)uracil.

Such a starting substance (I) is allowed to react with an organic sulfonylating agent (II) in the presence of potassium carbonate.

In the formula (II) of the organic sulfonylating agents, $R^3$ of the organic sulfonyl group ($R^3SO_2$) is illustrated by a lower alkyl group such as methyl, ethyl and n-propyl, or an aryl group such as phenyl and naphthyl. These lower alkyl groups and aryl groups may be substituted with halogen such as chlorine and fluorine, and the aryl groups may be substituted with $C_{1-3}$ alkyl or $C_{1-3}$ alkoxyl such as methyl, ethyl, isopropyl and methoxyl groups. The halogen atom reffered to in the definition of X in the formula may be chlorine or bromine, but it is usually chlorine. The sulfonylating agents (II) that can be used in this invention are exemplified by trifluoromethane sulfonyl chloride, benzene sulfonyl chloride, p-chlorobenzene sulfonyl chloride, p-toluene sulfonyl chloride, 4-methoxy-2,3,6-trimethylbenzene sufonyl chloride, p-methoxybenzene sulfonyl chloride, 2,4,6-trimethylbenzene sulfonyl chloride, 4-methoxy-2,6-dimethylbenzene sulfonyl chloride, 2,4,6-triisopropylbenzene sulfonyl chloride and 2,3,4,5,6-pentamethylbenzene sulfonyl chloride. In this invention it is desirable to use, among these sulfonylating agents, sulfonylating agents (II'), where $R^3$ is a benzene ring substituted with 1 to 5 members of the group of $C_{1-3}$ alkyl, such as methyl, isopropyl, and $C_{1-3}$ alkoxyl, such as methoxyl, and X is chlorine. One mole or more of such organic sulfonylating agent is sufficient, but usually 1 to 3 moles, preferably about 1.5 to 2 moles, is employed per mole of the starting substance (I).

The acid-eliminating agent, potassium carbonate ($K_2CO_3$), is used in the form of powders, and the smaller the particle size the higher the reaction-promotin effect. Usually powders of 30–300 mesh pass may be used. About 1 to 5 moles, preferably about 1.5 to 3 moles of such powders of potassium carbonate is used per mole of the starting substance (I).

The sulfonylation is carried out in an organic solvent. The solvents that can be used in this invention include ketones such as acetone, methylethylketone, and methylisobutylketone, esters such as ethyl acetate and butyl acetate, aromatic hydrocarbons such as benzene and toluene, ethers such as isopropylether, tetrahydrofuran and dioxane, halogenated hydrocarbons such as 1,2-dichloroethane, dichloromethane and chlorobenzene, and acetonitrile. Thus, an almost non-polar solvent such as halogenated hydrocarbons may be used in this invention. The amount of the solvent used usually about 5 to 100 parts by volume per one part by weight of the starting substance, preferably about 10 to 30 parts by volume, but is not necessarily limited in this range.

The sulfonylation is carried out at about 0°–150° C., preferably at room temperature to 100° C., and desirably by stirring at the reflux temperature of the solvent. The reaction is complete in about 0.5–10 hours.

By this reaction the desired substances 4-O-sulfonyluracil derivatives (II), are obtained. The extent of the progress of the reaction can be monitored for example by thin layer chromatography (TLC; Kieselgel 60F$_{254}$ plate: manufactured by Merck Co.; developing solvent: chloroform-acetone (6:1, v/v). The product (III) can be isolated for example by descending flush-chromatography (developing solvent: chloroform-acetone (4:1, v/v) using a column packed with silica gel. The structure of the desired substance thus isolated can be confirmed by NMR.

The uracil derivatives (III) are unstable in neutral or acidic conditions, and preferably are subjected to the subsequent reaction without being isolated from the reaction mixture. The reaction mixture contains precipitates derived from the acid-eliminating agent $K_2CO_3$ or the byproduct KCl, but the reaction mixture can be subjected to the subsequent amination at the position 4 without any further treatment or after removal of such precipitates for example by filtration.

4-O-sulfonyluracil derivatives (III) can be converted easily to cytosine derivatives by amination at the position 4.

For the amination, ammonia or primary or secondary amines may be used. In case of ammonia the O-sulfonyl group at the position 4 is substituted with the amino group, and in case of primary or secondary amines it is substituted with a substituted amino group. The primary amines include $C_{1-6}$ alkylamine whose alkyl moiety may be substituted by benzene or a di $C_{1-3}$ alkyl-substituted amino group, the $C_{1-6}$ alkylamine being, for example, methylamine, ethylamine, propylamine, butylamine, benzylamine, β-phenethylamine, 2-(3,4-dihydroxyphenyl)-ethylamine, homoveratrylamine, and N,N-dimethylethyenediamine. The secondary amines include di $C_{1-4}$ alkylamine such as dimethylamine, diethylamine, 5–7 membered alicyclic imino compounds which may have oxygen in the ring molecule in place of carbon, the 5–7 membered alicyclic imines being illustrated by pirrolidine, piperidine, morpholine and hexamethyleneimine. The amination reaction is carried out in an organic solvent. In order to accomplish effective amination, a solvent as is defined in the sulfonation process is preferably used. Ammonia, gaseous or dissolved in an organic solvent, in excess of the theoretical amount, is added all at once or little by little. About 2 to 5 moles of a primary or secondary amine per mole of sulfonyluracil derivative (III) is used. The amine also may be added all at once or little by little. The amination is usually carried out at 0°–150° C., preferably at room temperature to 50° C., and is complete in about 0.5–10 hours.

After completion of the amination, a protecting group for protection of the hydroxyl groups of the sugar moiety can be eliminated by a routine method such as hydrolysis and catalytic reduction, if necessary.

Cytosine derivatives thus produced can be isolated and purified by the conventional procedures usually used for isolation and purification, such as filtration, concentration, recrystallization, adsorption and ion exchange column chromatography.

The procedures (1) and (2) of this invention are industrially very useful because the desired substances can be obtained in a very high yield with industrially easily available solvents, reagents, and acid-eliminating agents; with the procedure (1) the reaction can proceed almost quantitatively and the reaction mixture can be used for the reaction in the procedure (2) without any further treatment. The yield in the procedures (1) and (2) is consistently more than about 90% of the amount of the material used, and thus the desired substance can be obtained in a very high yield. The use of a benzene sulfonyl chloride whose benzene ring is substituted with methyl or methoxy as the organic sulfonylating agent has an advantage that the cytosine derivative is obtained in a yield of 95% or more.

EXAMPLE 1

To a solution of 7.5 g (20.27 mmole) of 2',3',5'-tri-O-acetyluridine in 80 ml of methylisobutylketone, 8.4 g (60.8 mmole) of potassium carbonate powders of 30–50 mesh and 8.0 g (41.9 mmole) of p-toluene sulfonyl chloride were added and heated by stirring at 80° C. for 4 hours and then at 60° C. overnight. The resultant reaction mixture was cooled to room temperature, the insoluble matter was filtered off, and the filtrate was concentrated under reduced pressure. The desired centrate was submitted to column chromatography using silica gel (200 g) and chloroform-acetone (6:1, v/v). The aimed fractions were concentrated under reduced pressure, to give colorless oily 2',3',5'-tri-O-acetyl-4-O-(p-toluene sulfonyl)uridine. Yield: 10.2 g (97.7%)

$^{13}$C-NMR spectrum (heavy chloroform) δ (ppm): 153.50 (singlet, carbon at the position 2 in pyrimidine base moiety), 166.76 (singlet, carbon at the position 4 in pyrimidine base moiety), 95.93 (doublet, carbon at the position 5 in pyrimidine base moiety), 129.96 (doublet, carbon at the position 6 in pyrimidine base moiety).

EXAMPLE 2

To a solution of 7.5 g (20.27 mmole) of 2',3',5'-tri-O-acetyluridine in 80 ml of methylisobutylketone, 8.4 g (60.8 mmole) of potassium carbonate powders of 30–50 mesh and 8.0 g (41.9 mmole) of p-toluene sulfonyl chloride were added and heated by stirring at 80° C. for 4 hours and then at 60° C. overnight. The solution was cooled to room temperature, the insoluble matter was filtered off, and amount gas was sent into the filtrate by stirring at room temperature for one hour. After that, the reaction mixture was stirred at room temperature for 3 hours. The resultant insoluble matter was filtered off, and the filtrate was concentrated under reduced pressure.

To the concentrate, 200 ml of methanol and 50 ml of conc. ammonia water were added and allowed to stand at room temperature overnight. The solution was concentrated under reduced pressure, and to the concentrate 200 ml of water was added. The resultant precipitates were filtered off, and water was added to the filtrate to make 300.0 g. The amount of cytidine and that of uridine in this solution were quantitatively determined by high performance liquid chromatography (HPLC):

cytidine 4.50 g (91.4%)
uridine 0.403 g (8.1%).

EXAMPLE 3

To a solution of 3.7 g of 2',3',5'-tri-O-acetyluridine in 80 ml of 1,2-dichloroethane, 4.0 g of 4-methoxy-2,3,6-trimethylbenzene sulfonyl chloride and 2.8 g of potassium carbonate powders of 150 mesh were added and heated for 3 hours by stirring under reflux using a water separator. The reaction mixture was cooled to room temperature and filtered by using 3 g of filter aid (High Flow Super Cell ®; manufactured by Jones Manville Sales Co., Ltd.). Ammonia gas was introduced into the filtrate with stirring at 0° C. for one hour.

After introduction of ammonia gas, the reaction mixture was mixed by stirring at room temperature for 3 hours, at 30° C. for 2 hours and 40° C. for one hour, and then filtered by using 2 g of filter aid (High Flow Super Cell ®). The filtrate was concentrated under reduced pressure. To the concentrate 60 ml of methanol and 20 ml of conc. ammonia water were added and warmed at 40° C. for 2 hours. The solution was concentrated under reduced pressure, and to the concentrate water was added to make 101.20 g. The amount of cytidine and that of uridine in this solution were quantitatively determined by HPLC.

cytidine 2.27 g (92.7%)
uridine 0.149 g (6.0%).

REFERENCE 1

A solution containing cytidine and uridine obtained in the same way as in Example 3, 1010 g (containing 21.8 g of cytidine), was charged on a column packed with 300 ml of ion exchange resin (Dia Ion ®SK-110; manufactured by Mitsubishi Chemical Industries Ltd.) and the column was then washed with 300 ml of water. Elution was carried out with 600 ml of 2N ammonia water and then with water, to give 1500 ml of main eluate. This main eluate was concentrated under reduced pressure until vigorous bubbling appeared, and cooled at 5° C. overnight after addition of 100 ml of methanol. The resultant cytidine crystals were obtained by filtration, washed with cold methanol and dried. Yield: 21.0 g (recovery 96.3%)

EXAMPLE 4

To a solution of 3.7 g of 2',3',5'-tri-O-acetyluridine in 80 ml of 1,2-dichloroethane, 4.0 g of 4-methoxy-2,3,6-trimethylbenzene sulfonyl chloride and 2.8 g of potassium carbonate powders of 150 mesh were added and heated by stirring under reflux for 4 hours using water separator. A reaction mixture was cooled to room temperature and filtered by using 2 g of filter aid (High Flow Super Cell ®). Into the filtrate ammonia gas was introduced with stirring at room temperature for one hours. After completion of the introduction of ammonia, the reaction mixture was stirred at 40° C. for 8 hours. To the reaction mixture, 50 ml of water and 50 ml of conc. ammonia water were added and stirred at room temperature overnight so that the organic phase and the aqueous phase might be mixed thoroughly. The reaction mixture was allowed to stand and separate into phases. The aqueous phase separated was concentrated under reduced pressure to some extent and water was added to the concentrate to make 104.61 g. The amount of cytidine and that of uridine were quantitatively analyzed by HPLC.

cytidine 2.32 g (94.7%)
uridine 0.125 g (5.1%).

REFERENCE 2

A solution containing cytidine and uridine obtained in the same way as in Example 4, 1046 g (containing 22.8 g of cytidine) was charged on a column packed with 1300 ml of adsorption resin (Super-beads ®SP 207; manufactured by Mitsubishi Chemical Industries Ltd.). Elution was carried out with 1950 ml of 2N ammonia water and then with distilled water, to give eluate containing cytidine. The eluate was concentrated until vigorous bubbling was observed, 100 ml of methanol was added, and the mixture was allowed to stand at 5° C. overnight. The resultant precipitate cytidine crystals, were obtained by filtration, washed with methanol and dried. Yield: 21.9 g (recovery 96.1%)

EXAMPLE 5

To a solution of 3.88 g of 2',3',5'-tri-O-acetyl-5-fluorouridine in 80 ml of 1,2-dichloroethane, 2.77 g of potassium carbonate powders of 150 mesh and 3.81 g of p-toluene sulfonyl chloride were added and heated for 4 hours by stirring under reflux with a water separator. After cooling to room temperature, the reaction mixture was filtered by using 2.0 g of filter aid (High Flow Super Cell ®). Into the filtrate ammonia gas was introduced with stirring at room temperature for one hour. After completion of the introduction of ammonia gas, the reaction mixture was allowed to stand at room temperature overnight. To the reaction mixture, 50 ml of water and 50 ml of ammonia water were added and stirred at room temperature overnight so that the organic phase and the aqueous phase might be mixed thoroughly. The resulting reaction mixture was allowed to stand, and the aqueous phase was separated. The aqueous phase was concentrated under reduced pressure, and water was added to the concentrate to make 50.02 g. The amount of 5-fluorocytidine in the solution was determined by HPLC. Yield of 5-fluorocytidine was 2.41 g (92.3%).

EXAMPLE 6

To a solution of 3.84 g of 2',3',5'-tri-O-acetyl-5-methyluridine in 80 ml of 1,2-dichloroethane, 2.77 g of potassium carbonate powders of 150 mesh and 3.81 g of p-toluene sulfonyl chloride were added and heated for 4 hours by stirring under reflux with a water separator. After cooling to room temperature, the reaction mixture was filtered by using 2.0 g of filter aid (High Flow Super Cell ®). Into the filtrate ammonia gas was introduced with stirring at room temperature for one hour. After completion of the intriduction of ammonia gas, the reaction mixture was allowed to stand at room temperature overnight. To the reaction mixture, 50 ml of water and 50 ml of conc. ammonia water were added and stirred at room temperature overnight so that the organic phase and the aqueous phase might be mixed thoroughly. The resulting reaction mixture was allowed to stand, and the aqueous phase was separated. The aqueous phase was concentrated under reduced pressure and water was added to the concentrate to make 50.01 g. The amount of 5-methylcytidine in the solution was determined by HPLC. Yield of 5-methylcytidine was 2.32 g (90.3%).

EXAMPLE 7

To a solution of 3.71 g of 2',3',5'-tri-O-acetyluridine in 80 ml of 1,2-dichloroethane, 2.77 g of potassium carbonate powders of 150 mesh and 3.81 g of p-toluene sulfonyl chloride were added and heated for 4 hours by stirring under reflux with a water separator. After cooling to room temperature, the reaction mixture was filtered by using 2.0 g of filter aid (High Flow Super Cell ®). To the filtrate 5.0 g of β-phenethylamine was added and stirred at room temperature overnight. To the reaction mixture, 100 ml of water and 50 ml of conc. ammonia water were added, and stirred at room temperature overnight so that the aqueous phase and the organic phase might be mixed thoroughly. The resulting reaction mixture was allowed to stand, and the aqueous phase was separated. The aqueous phase was concentrated under reduced pressure, and water was added to the concentrate to make 100.01 g. The amount of 4-N-(2-phenylethyl)cytidine in the solution was determined by HPLC. Yield of 4-N-(2-phenylethyl)cytidine was 3.15 g (90.8%).

EXAMPLE 8

To a solution of 3.71 g of 2',3',5'-tri-O-acetyluridine in 80 ml of 1,2-dichloroethane, 2.77 g of potassium carbonate powders of 150 mesh and 3.81 g of p-toluene sulfonyl chloride were added and heated for 4 hours by stirring under reflux with a water separator. After cooling to room temperature, the reaction mixture was filtered by using 2.0 g of filter aid (High Flow Super Cell ®). To the filtrate, 2.85 g of pyrrolidine was added and stirred at room temperature overnight. To the reaction mixture 50 ml of water and 50 ml of conc. ammonia water were added, and stirred at room temperature so that the aqueous phase and the organic phase might be mixed thoroughly. The resulting reaction mixture was allowed to stand and the aqueous phase was separated. The aqueous phase was concentrated under reduced pressure, and water was added to the concentrate to make 75.01 g. The amount of 4-N,N-tetramethylenecytidine was determined by HPLC. Yield of 4-N,N-tetramethylenecytidine was 2.68 g (91.5%).

EXAMPLE 9

To a solution of 3.71 g of 1-(2',3',5'-tri-O-acetyl-β-D-arabinofuranosyl)uracil in 80 ml of 1,2-dichloroethane, 2.77 g of potassium carbonate powders of 150 mesh and 3.81 g of p-toluene sulfonyl chloride were added, and heated for 4 hours by stirring under reflux with a water separator. After cooling to room temperature, the reaction mixture was filtered by using 2.0 g of filter aid (High Flow Super Cell ®). To the filtrate ammonia gas was introduced with stirring at room temperature for one hour. After completion of the introduction of ammonia gas, the reaction mixture was kept still at room temperature overnight. To the resultant reaction mixture 50 ml of water and 50 ml of conc. ammonia water were added and stirred at room temperature overnight so that the organic phase and the aqueous phase might be mixed thoroughly. The reaction mixture was kept still and the aqueous phase was separated. The aqueous phase was concentrated under reduced pressure, and water was added to the concentrate to make 50.00 g. The amount of 1-β-D-arabinofuranosyl cytosine in this solution was determined by HPLC. Yield of 1-β-D-arabinofuranosyl cytosine was 2.21 g (91.0%).

EXAMPLE 10

To a solution of 3.12 g of 1-(2'-deoxy-3', 5'-di-O-acetyl-β-D-ribofuranosyl)uridine in 80 ml of 1,2-dichloroethane, 2.77 g of potassium carbonate powders of 150 mesh and 3.81 g of p-toluene sulfonyl chloride were added, and heated for 4 hours by stirring under reflux with a water separator. After cooling to room temperature, the reaction mixture was filtered by using 2.0 g of filter aid (High Flow Super Cell ®). To the filtrate ammonia gas was introduced with stirring at room temperature for one hour. After completion of the introduction of ammonia gas, the reaction mixture was kept still at room temperature overnight. To the reaction mixture 50 ml of water and 50 ml of conc. ammonia water were added and stirred at room temperature overnight so that the organic phase and the aqueous phase might be mixed thoroughly. The resultant reaction mixture was kept still, and the aqueous phase was separated. The aqueous phase was concentrated under reduced pressure, and water was added to the concentrate to make 60.01 g. The amount of 1-(2'-deoxy-β-D-ribofuranosyl)cytosine was determined by HPLC.

Yield of 1-(2'-deoxy-β-D-ribofuranosyl)cytosine was 2.06 g (90.7%).

EXAMPLE 11

A mixture of 3.80 g of 2',3',5'-tri-O-acetyluridine, 3.11 g of p-methoxybenzene sulfonyl chloride, 2.1 g of potassium carbonate powders and 80 ml of acetonitrile was heated at 50° C. for one hour and then at 60° C. for 4 hours under stirring. Into the reaction mixture, ammonia gas was introduced at 50° C. for one hour. After mixing the reaction mixture at 50° C. for 2 hours, the insoluble matter was filtered off. The filtrate was concentrated under reduced pressure. The concentrate to which 30 ml of methanol and 15 ml of conc. ammonia water were added was allowed to stand at room temperature overnight. The reaction solution was concentrated under reduced pressure, and water was added thereto. The precipitates separated were filtered off. To the filtrate water was added to make 166.96 g in total. The amount of cytidine and uridine were determined by HPLC.

Cytidine 2.37 g (96.2%)
Uridine 0.088 g (3.6%).

EXAMPLE 12

A mixture of 3.80 g of 2',3',5'-tri-O-acetyluridine, 3.28 g of 2,4,6-trimethylbenzene sulfonyl chloride, 2.11 g of potassium carbonate powders and 80 ml of acetonitrile was heated at 50° for 5 hours and then at 60° C. for 3 hours under stirring. Into the reaction mixture, ammonia gas was introduced at 50° C. for one hour. After mixing the reaction mixture at 50° C. for 30 minutes, the insoluble matter was filtered off. The filtrate was concentrated under reduced pressure. The concentrate, to which 30 ml of methanol and 15 ml of conc. ammonia water were added, was allowed to stand at room temperature overnight. The reaction solution was concentrated under reduced pressure, and water was added thereto. The precipitates separated were filtered off. To the filtrate, water was added to make 207.58 g in total. The amounts of cytidine and uridine were determined by HPLC.

Cytidine 2.381 g (96.5%)
Uridine 0.109 g (4.4%).

EXAMPLE 13

A mixture of 7.89 g of 2',3',5'-tri-O-acetyluridine, 10.0 g of 4-methoxy-2,6-dimethylbenzene sulfonyl chloride, 5.94 g of potassium carbonate and 160 ml of acetonitrile was heated at 50° C. for 6 hours under stirring. Into the reaction mixture, ammonia gas was introduced at 50° C. for one hour. The reaction mixture was allowed to satnd at room temperature overnight and the precipitates were filtered off. The filtrate was concentrated under reduced pressure. The concentrate, to which 60 ml of methanol and 30 ml of conc. ammonia water were added, was allowed to stand at room temperature overnight. The reaction solution was concentrated under reduced pressure, and water was added thereto. The precipitates separated were filtered off. To the filtrate water was added to make 231.77 g in total. The amounts of cytidine and uridine in the solution were determined by HPLC.

Cytidine 4.867 g (94.0%)
Uridine 0.193 g (3.7%).

EXAMPLE 14

A mixture of 3.80 g of 2',3',5'-tri-O-acetyluridine, 4.53 g of 2,4,6-triisopropylbenzene sulfonyl chloride, 2.10 g of potassium carbonate powders and 80 ml of acetonitrile was heated at 50° C. for 2 hours under stirring. Into the reaction mixture, ammonia gas was introduced at 50° C. for one hour. After mixing the reaction mixture at 50° C. for 2.5 hours, the insoluble matter was filtered off. The filtrate was concentrated under reduced pressure. The concentrate, to which 30 ml of methanol and 15 ml of conc. ammonia water were added, was allowed to stand at room temperature for two days. The reaction solution was concentrated under reduced pressure, and water was added thereto. The precipitates separated were filtered off. To the filtrate water was added to make 195.49 g in total. The amounts of cytidine and uridine were determined by HPLC.

Cytidine 2.367 g (95.9%)
Uridine 0.1081 g (4.4%).

EXAMPLE 15

A mixture of 3.80 g of 2',3',5'-tri-O-acetyluridine, 3.70 g of 2,3,4,5,6-pentamethylbenzene sulfonyl chloride, 2.10 g of potassium carbonate powders and 80 ml of acetonitrile was heated at 50° C. for one hour under stirring. Into the reaction mixture, ammonia gas was introduced at 50° C. for one hour. The insoluble matter was filtered off. The filtrate was concentrated under reduced pressure. The concentrate, to which 30 ml of methanol and 15 ml of conc. ammonia water were added, was allowed to stand at room temperature overnight. The reaction solution was concentrated under reduced pressure, and water was added thereto. The precipitates separated were filtered off. To the filtrate water was added to make 159.94 g in total. The amounts of cytidine and uridine were determined by HPLC.

Cytidine 2.382 g (96.5%)
Uridine 0.111 g (4.5%).

We claim:

1. A process for producing a cytosine derivative which comprises:
   (i) producing a 4-O-sulfonyluracil derivative having the formula:

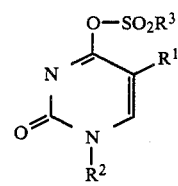

wherein $R^1$ is a hydrogen atom, a halogen atom, an alkyl group or an alkoxyl group, $R^2$ is a glycosyl group whose hydroxyl groups are protected, and $R^3SO_2$ is an organic sulfonyl group by reacting a uracil derivative having the formula:

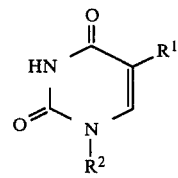

wherein R¹ and R² are as defined above with an organic sulfonylating agent having the formula R³SO₂X wherein R³SO₂ is an organic sulfonyl group and X is a halogen atom in the presence of potassium carbonate, and (ii) subjecting the 4-O-sulfonyluracil derivative obtained in step (i) to amination.

2. A process according to claim 1, wherein the amination is carried out with ammonia or a primary or secondary amine.

3. A process according to claim 2, wherein the primary or secondary amine in step (ii) is a primary amine of $C_{1-6}$ alkylamine or secondary amine of di-$C_{1-4}$ alkylamine or 5–7 membered alicyclic imine which may have oxygen in the ring molecule in place of carbon.

4. A process according to claim 1, wherein the objective cytosine derivative is represented by the formula:

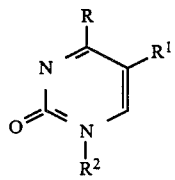

wherein R is an amino group, $C_{1-6}$ alkylamino group, di-$C_{1-4}$ alkylamino group or 5–7 membered alicyclic imino group which may have oxygen in the ring molecule in place of carbon, R¹ is a hydrogen atom, a halogen atom, an alkyl group or an alkoxyl group and R² is a glycosyl group whose hydroxyl groups may be protected.

5. A process according to claim 1, wherein the uracil derivative to be reacted with the organic sulfonylating agent in step (i) is ribofuranosyluracil in which the hydroxyl groups of ribofuranosyl are protected.

6. A process according to claim 1, wherein in the organic sulfonylating agent, R³ is a benzene ring substituted by 1 to 5 members of the group $C_{1-3}$ alkyl and $C_{1-3}$ alkoxy and X is chlorine.

7. A process according to claim 1, wherein the reaction is steps (i) and (ii) is carried out in the presence of an organic solvent.

8. A process according to claim 1, wherein the sulfonylating agent is used in amount of 1 to 3 moles per mole of the starting uracil derivatives.

9. A process according to claim 1, wherein the acid-eliminating agent, potassium carbonate, is used in an amount of about 1 to 5 moles per mole of the starting uracil derivative.

10. A process according to claim 1, wherein the reaction in steps (i) and (ii) is carried out at the temperature of 0° to 150° C.

11. A process according to claim 1 wherein subsequent to amination, the resultant product is subjected to hydrolysis or catalytic reduction to eliminate the protecting groups of the hydroxy groups in the glycosyl moiety.

12. A process for producing a 4-O-sulfonyluracil derivative having the formula

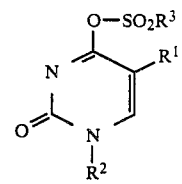

wherein R¹ is a hydrogen atom, a halogen atom, an alkyl group or an alkoxyl group, R² is a glycosyl group whose hydroxyl groups are protected, and R³SO₂ is an organic sulfonyl group which comprises reacting an uracil derivative having the formula

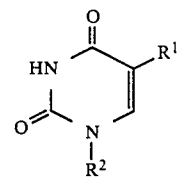

wherein R¹ and R² are as defined above with an organic sulfonylating agent having the formula R³SO₂X wherein R³SO₂ is an organic sulfonyl group and X is a halogen atom in the presence of potassium carbonate.

13. A process according to claim 12, wherein the uracil derivative to be reacted with the organic sulfonylating agent is ribofuranosyluracil in which the hydroxyl groups of ribofuranosyl are protected.

14. A process according to claim 12, wherein in the organic sulfonylating agent, R₃ is a benzene ring substituted by 1 to 5 members of the group $C_{1-3}$ alkyl and $C_{1-3}$ alkoxy and X is chlorine.

15. A process according to claim 12, wherein the reaction is carried out in the presence of an organic solvent.

16. A process according to claim 12, wherein the sulfonylating agent is used in an amount of 1 to 3 moles per mole of the starting uracil derivatives.

17. A process according to claim 12, wherein the acid-eliminating agent, potassium carbonate, is used in an amount of about 1 to 5 moles per mole of the starting uracil derivative.

18. A process according to claim 12, wherein the reaction is carried out at the temperature of 0° to 150° C.

* * * * *